United States Patent [19]

Gulavita et al.

[11] Patent Number: 5,516,755
[45] Date of Patent: May 14, 1996

[54] ANTITUMOR AND ANTIBACTERIAL PEPTIDE AND METHODS OF USE

[75] Inventors: Nanda K. Gulavita, Palm Bay; Sarath P. Gunasekera, Vero Beach; Shirley A. Pomponi, Fort Pierce; Ross E. Longley; Peter J. McCarthy, both of Vero Beach, all of Fla.

[73] Assignee: Harbor Branch Oceanographic Institution, Inc., Ft. Pierce, Fla.

[21] Appl. No.: 287,021

[22] Filed: Aug. 8, 1994

Related U.S. Application Data

[62] Division of Ser. No. 831,137, Feb. 7, 1992, Pat. No. 5,336,757.

[51] Int. Cl.$^6$ .................. A61K 38/00; A61K 38/02; C04K 5/00; C04K 7/00
[52] U.S. Cl. .................. 514/11; 514/9; 530/317
[58] Field of Search .................. 530/317; 514/9, 514/11

[56] References Cited

U.S. PATENT DOCUMENTS

| | | | |
|---|---|---|---|
| 4,548,814 | 10/1985 | Rinehart, Jr. ............... | 424/95 |
| 4,729,996 | 3/1988 | Wright et al. ............... | 514/215 |
| 4,737,510 | 4/1988 | Rinehart, Jr. ............... | 514/388 |
| 4,808,590 | 2/1989 | Higa et al. ............... | 514/272 |
| 5,336,757 | 8/1994 | Gulavita et al. ............... | 530/317 |

OTHER PUBLICATIONS

Uemura et al., *J. Am. Chem. Soc.*, vol. 107, pp. 4796–4798, 1985.

Faulkner, D. J. (1984) "Marine Natural Products: Metabolites of Marine Invertebrates" Natural Products Reports 1:551–598.

Faulkner, D. J. (1986) "Marine Natural Products" Natural Products Reports 3:1–33.

Faulkner, D. J. (1987) "Marine Natural Products" Natural Products Reports 4:539–576.

Uemura, Daisuke et al. (1985) "Norhalichondrin A: An Antitumor Polyeter Macrolide from a Marine Sponge" J. Am. Chem. Soc. 107:4796–4798.

Matsunaga, S. et al. (1984) "Bioactive Marine Metabolites VI Structure Elucidation of Discodermin A. An Antimicrobial Peptide from the Marine Sponge *Discodermia kilensis*" Tetrahedron Letters 25(45):5165–5168.

Matsunaga, S. et al. (1985) "Bioactive Marine Metabolites VII Structures of Discodermins B, C, and D, Antimicrobial Peptides from the Marine Sponge *Discodermia kiiensis*" Tetrahedron Letters 26(7):855–856.

Matsunaga, S. et al. (1985) "Bioactive Marine Metabolites, IV. Isolation and the amino acid composition of discodermin A, an antimicrobial peptide, from the marine sponge *Discodermia kilensis*" Journal of Natural Products 48(2):236–241.

*Primary Examiner*—Christina Y. Chan
*Assistant Examiner*—A. M. Davenport
*Attorney, Agent, or Firm*—Saliwanchik & Saliwanchik

[57] ABSTRACT

A novel peptide, polydiscamide A, has been isolated from a marine sponge. This compound, and its derivatives, are useful as antibacterial and antitumor agents.

5 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single (D) TOPOLOGY: linear (ii) MOLECULE TYPE: peptide (iii) HYPOTHETICAL: NO (iv) ANTI-SENSE: NO (vi) ORIGINAL SOURCE:
    (A) ORGANISM: Discodermia (xi) SEQUENCE DESCRIPTION: SEQ ID NO:1:

Ala  Xaa  Xaa  Xaa  Xaa  Trp  Arg  Xaa  Thr  Xaa  Val  Xaa  Asn
 1                     5                      10

ANTITUMOR AND ANTIBACTERIAL PEPTIDE AND METHODS OF USE

This is a division of application Ser. No. 07/831,137, filed Feb. 7, 1992 and now U.S. Pat. No. 5,336,757.

BACKGROUND OF THE INVENTION

Considerable research and resources have been devoted to oncology and antitumor measures including chemotherapy. While certain methods and chemical compositions have been developed which aid in inhibiting, remitting, or controlling the growth of tumors, new methods and antitumor chemical compositions are needed. The prevention and control of bacterial growth is also of considerable importance to man, and much research has been devoted to development of antibacterial measures.

It has been found that some natural products and organisms are potential sources for chemical molecules having useful biological activity of great diversity. Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge *Theonella sp.*; and U.S. Pat. No. 4,737,510 discloses compounds, having antiviral and antibacterial properties, isolated from the Caribbean sponge *Agelas coniferin*. Clearly, marine sponges have proved to be a source of biological compounds, and a number of publications have issued disclosing organic compounds derived from marine sponges, including Scheuer, P. J. (ed.) Marine Natural Products, Chemical and Biological Perspectives, Academic Press, New York, 1978–1983, Vol. I–V; Faulkner, D. J., (1984) Natural Products Reports 1:551–598; Natural Products Reports (1986) 3:1–33; Natural Products Reports (1987) 4:539–576; J. Am. Chem. Soc. (1985) 107:4796–4798.

The subject invention concerns novel polydiscamide A. The parent compound was isolated from a previously undescribed marine sponge of the genus Discodermia. Discodermines A-D have previously been isolated from a different sponge *Discodermia kiiensis*. The type of amino acids, sequence of amino acids, and the ring size of the macrocyclic ring are completely different from the reported Discodermines A-D. See Matsunaga, S., N. Fusetani, S. Konosu (1985) J. Nat. Prod. 48:236; Matsunaga, S., N. Fusetani, S. Konosu (1984) Tetrahedron Lett. 25:5165; and Matsunaga, S., N. Fusetani, S. Konosu (1985) Tetrahedron Lett. 26:855. The compounds claimed here have never before been described. The present invention, utilizing sponges as a source material has provided the art with a new class of biologically active compounds and new pharmaceutical compositions useful as antitumor and antibacterial agents.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The subject invention concerns novel peptides, polydiscamides, and methods of use for these compounds. Specifically exemplified is polydiscamide A which is a depsipeptide containing thirteen amino acids (SEQ ID NO. 1). The structure of polydiscamide A and its analogs is shown in FIG. 1.

Polydiscamide A has been found to inhibit tumor cell growth. This compound, and derivatives thereof, is therefore useful in the treatment of cancer in animals and humans.

The compounds of the subject invention can also be used to inhibit bacterial growth and, therefore, can be used in the treatment of certain diseases in humans, animals, and plants.

BRIEF DESCRIPTION OF THE SEQUENCE

Figure 1:
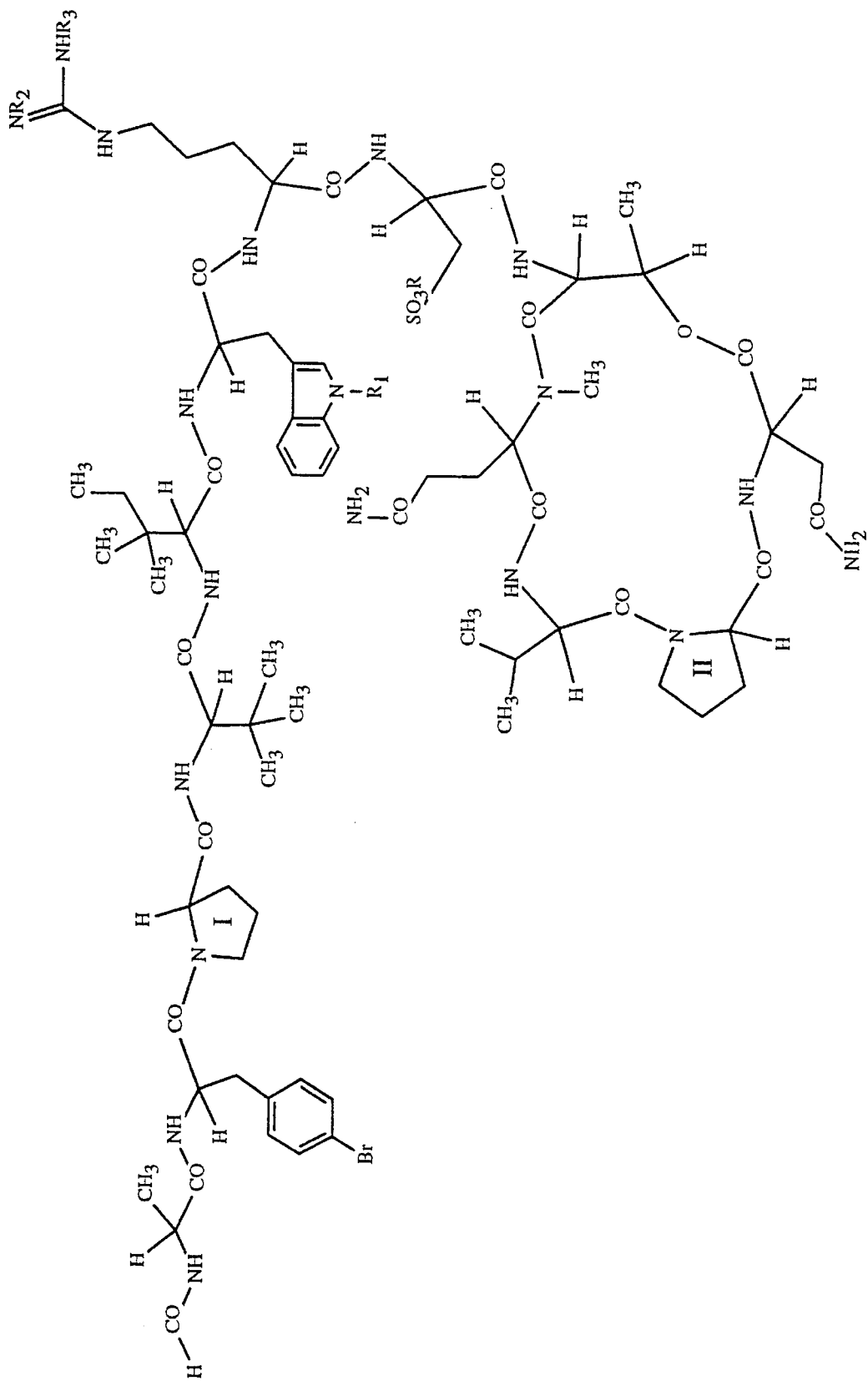
FIG. 1 shows the structure of polydiscamide A and its analogs. Polydiscamide A is a depsipeptide containing thirteen amino acids. The various analogs of polydiscamide A comprise the structure wherein $R_1=R_2=R_3=H$ or Ac and R=Na, H, or $CH_3$. The preferred embodiment, polydiscamide A, comprises $R_1=R_2=R_3=H$; R=Na.

SEQ ID NO. 1 is the amino acid sequence for polydiscamide A.

DETAILED DISCLOSURE OF THE INVENTION

The subject invention pertains to a novel chemical compound which can be isolated from marine sponges. Derivatives of this compound are also described and claimed. These compounds have been shown to possess antitumor and antibacterial activity. Thus, the subject invention pertains to the compounds themselves, as well as pharmaceutical compositions containing these compounds. Also disclosed and claimed are methods for administering the novel compositions. The derivatives of these compounds can be produced by known procedures. The parent compound can be isolated from marine sponges as described below.

The isolation of the natural product, polydiscamide A, was performed using solvent partition followed by chromatography. The final purification of the novel compound can be achieved either by crystallization or by using HPLC. The structure of polydiscamide A was determined mainly on the basis of its $^1H$ and $^{13}C$ NMR data.

A preferred embodiment of the subject invention is polydiscamide A, which comprises the structure shown in FIG. 1 wherein the R groups are defined as follows: R=Na and $R_1=R_2=R_3=H$. Other embodiments of the structure or analogs of polydiscamide A comprise R=H or $CH_3$. Additionally, derivatives of polydiscamide A can be prepared by replacing $R_1$, $R_2$, and $R_3$ with an acetyl (Ac) group via standard acetylation reactions.

All embodiments and derivatives of polydiscamide A can be prepared by using standard reactions and procedures which are well known to those skilled in the art. The specific reactions are described in more detail below (see Example 6 - Analogs and Variants of the Compound).

The 3-methyl isoleucine unit in polydiscamide A is an amino acid which has not previously been isolated from a natural source. The p-bromo phenylalanine unit is uncommon in naturally occurring peptides.

The compounds of the subject invention, including derivatives thereof, have antitumor and antibacterial properties. Thus, they can be used for the treatment of a number of diseases including cancer.

Following are examples which illustrate procedures, including the best mode, for practicing the invention. These examples should not be construed as limiting. All percentages are by weight and all solvent mixture proportions are by volume unless otherwise noted.

EXAMPLE 1 - IDENTIFICATION AND LOCATION OF MARINE SPONGE

The sponge of interest, *Discodermia sp.* (order Lithistida), can be collected on rock substrate off St. Lucia, Lesser Antilles, at a depth of 274 m. The sponge is of beige-white color and consists of firm, hollow tubes (1–3 cm diameter) which branch from a central stalk. The branches may have a single, apical oscule. This undescribed species of Discodermia was originally field-identified as *D. polydiscus*, but was subsequently found to be an undescribed species. The sponge has been classified as follows:

Phylum: Porifera
Class: Demospongiae
Order: Lithistida
Family: Theonellidae
Genus: Discodermia
Species: (previously undescribed)

The sponge from which the parent compound was isolated is similar to *D. polydiscus* in consistency and chemistry. Both species are hard in consistency as a result of skeletal architecture of the spicules: the desmas are arranged in an intricate, interconnecting network in *D. polydiscus* and less so in *Discodermia sp.* Polydiscamide A was found in samples of both species. Differences between *Discodermia sp.* and *D. potydiscus* are in morphology (hollow branching vs. spherical to lobate) and the spicule shape (round vs. irregular discotriaenes, a spicule that is diagnostic for the genus). A taxonomic voucher specimen of the sample of *Discodermia sp.* from which the polydiscamide A was isolated is deposited at the Harbor Branch Oceanographic Museum (catalog number 003:00145).

EXAMPLE 2 - ISOLATION OF COMPOUND

*Discodermia sp.* (1107 g wet sponge) was soaked in MeOH (2L) overnight, ground in a blender, and filtered. The residue was successively extracted with MeOH (1L), MeOH/EtOAc (500 mL/500 mL), EtOAc (2×1L). The MeOH extracts were combined, concentrated to a gum (35 g), and partitioned between EtOAc and water (4×500 mL:500 mL). The aqueous layer was concentrated to dryness, triturated with MeOH, and filtered. The filtrate was concentrated to dryness (14.1 g). A portion (5.5 g) was dissolved in MeOH/water (1:1) and chromatographed on reversed-phase $C_{18}$ column under vacuum with MeOH/water (1:1), followed by MeOH/water (8:2), and MeOH. The fraction that eluted with MeOH/water (8:2) was concentrated to dryness (600 mg), and rechromatographed on an RP-$C_{18}$ cartridge with MeOH. This fraction was concentrated to dryness and purified by HPLC on Dynamax Macro reversed-phase $C_{18}$ column with MeOH/water (8:2) containing acetic acid (2.2 mL/L of solution) to yield polydiscamide A (188 mg, 0.05% of wet weight). Polydiscamide A was found to have the following characteristics: white powder; mp 212–216 C; $[\alpha]^{24}_D$ -1.1 (c=1.89, MeOH): UV $\lambda_{max}$ nm ($\epsilon$) 214 (44900), 272 (5300), 280 (5400), 288 (4600); IR (KBr) 3300 (br), 1754 (sh), 1704 (sh), 1614 (br) cm$^{-1}$; $^1$H and $^{13}$CNMR Table 1; LRFABMS m/z (% relative intensity) 1733 (17.1), 1731 (16.7), 1071 (6.7), 1047 (4.8) HRFABMS m/z 1733.7045 (M+2H), calculated for $C_{75}H_{111}N_{19}O_{20}S^{81}BrNa$ 1733.7031 (1.4 mmu).

The bioactive peptide, polydiscamide A, is the major peptide present in the organism and can be isolated in pure form with about 0.05% yield with respect to the wet weight of the sponge. Large scale isolation can be done by using RP-18 vacuum liquid chromatography on the water extract (which can be obtained after partitioning the methanol extract with water/ethyl acetate) followed by RP-18 HPLC on a preparative column. All the necessary material for this process is readily available to a person skilled in this art.

EXAMPLE 3 - CHARACTERIZATION OF COMPUND

Characterization of polydiscamide A was determined by NMR spectral analysis. The results of these data are shown in Table 1, below.

TABLE 1

$^{13}$C and $^1$H NMR Data for Polydiscamide A

| | DMSO-d$_6$/TFA | | CD$_3$OD | |
|---|---|---|---|---|
| | $^{13}$C | $^1$H | $^{13}$C | $^1$H |
| Ala | | | | |
| α | 46.52 (d) | 4.31(m) | 48.87 | 4.35(q, 7.2) |
| β | 18.49 (q) | 0.94(d, 7.0) | 18.49 | 1.11(d, 7.1) |
| NCHO | 160.61 (d) | 7.90(s) | 163.40 | 8.00(s) |
| NH | — | 8.12(d, 7.8) | — | — |
| BrPhe | | | | |
| α | 51.53 (d) | 4.70(ddd, 10.5, 8.5, 2.3) | 53.55 | 4.85(dd, 4.4, 9.7) |
| β | 36.34 (t) | 2.70(dd, 13.8, 10.5) 2.97(dd, 13.8, 2.3) | 37.76 | 2.81(dd, 9.7, 14.2) 3.12(dd, 4.4, 14.2) |
| C4 | 136.16 (s) | — | 137.72 | — |
| C5/C9 | 131.68 (d) | 7.21(2H, d, 8.3) | 132.66 | 7.16(2H, d, 8.4) |
| C6/C8 | 130.80 (d) | 7.39(2H, d, 8.3) | 132.46 | 7.40(2H, d, 8.4) |
| C7 | 119.49 (s) | — | 121.55 | — |
| NH | — | 8.33(d, 8.5) | — | — |
| Pro I | | | | |
| α | 60.55 (d) | 4.54 | 61.65 | 4.60(dd, 4.0, 8.2) |
| β | 29.51$^b$ (t) | 2.12(m), 1.89(m) | 30.92 | 2.25(m), 2.07(m) |

TABLE 1-continued

| | $^{13}$C and $^1$H NMR Data for Polydiscamide A | | | |
|---|---|---|---|---|
| | DMSO-d$_6$/TFA | | CD$_3$OD | |
| | $^{13}$C | $^1$H | $^{13}$C | $^1$H |
| γ | 24.16 (t) | 1.88(m) | 25.66 | 1.99(m) |
| δ | 46.95 (t) | 3.62(2H, m) | 48.62 | 3.74(m), 3.61(m) |
| (t)-Leu | | | | |
| α | 59.46 (d) | 4.51(d, 10) | 61.56 | 4.49(s) |
| β | 35.12 (s) | — | 36.56 | — |
| γ | 26.72 (q) | 0.89(9H, s) | 27.50 | 1.01(9H, s) |
| NH | — | 7.70(d, 10) | — | |
| 3-Me Ile | | | | |
| α | 59.75$^c$ (d) | 4.13(d, 7.5) | 62.75 | 4.09(s) |
| β | 35.86 (s) | — | 36.90 | — |
| γ | 31.12 (t) | 1.06(m) | 32.77 | 1.12(m) |
| δ | 7.89 (q) | 0.62(t, 7.2) | 8.35 | 0.69(t, 7.3) |
| γ' | 22.71 (q) | 0.62(s) | 23.27 | 0.67(s) |
| γ" | 22.99 (q) | 0.73(s) | 23.60 | 0.80(s) |
| NH | — | 7.81(d, 7.5) | — | — |
| Trp | | | | |
| α | 53.71 (d) | 4.61(m) | 55.81 | 4.74(m) |
| β | 27.58 (t) | 3.16(dd, 5, 14) 2.92(m) | 28.35 | 4.41(dd, 6.0, 14.8), 3.12(m) |
| C4 | 109.87 (s) | — | 111.32 | — |
| C5 | 124.02 (d) | 7.13(s) | 124.98 | 7.15(s) |
| C6 | 137.04 (s) | — | 138.18 | — |
| C7 | 127.12 (s) | — | 128.62 | — |
| C8 | 118.32 (d) | 7.56(d, 7.8) | 119.46 | 7.57(d, 7.7) |
| C9 | 118.14 (d) | 6.94(t, 7.4) | 119.83 | 6.98(dd, 7.4, 7.7) |
| C10 | 120.77 (d) | 7.02(t, 7.4) | 122.44 | 7.07(dd, 7.3, 8.1) |
| C11 | 111.22 (d) | 7.31(d, 8.1) | 112.33 | 7.32(d, 8.1) |
| NH | — | 8.17(d, 7.3) | — | — |
| NH—Aromatic | — | 10.63(br s) | — | — |
| Arg | | | | |
| α | 52.19 (d) | 4.31(m) | 54.72 | 4.39(m) |
| β | 28.83 (t) | 1.61(br, m) | 30.07 | 1.83(m), 1.67(m) |
| γ | 23.60 (t) | 1.32(br, m) | 25.53 | 1.49(m), 1.41(m) |
| δ | 40.26 (t) | 2.99(m) | 41.90 | 3.09(m) |
| guan | 156.76 (s) | — | 158.53 | — |
| NH | — | 8.00(d, 7.3) | — | — |
| Cysteic acid | | | | |
| α | 50.81 (d) | 4.63(m) | 52.68 | 4.79(dd, 4.2, 9.2) |
| β | 52.19 (t) | 2.95(m) | 52.01 | 3.26(dd, 4.2, 14.1) 3.34(dd, 9.2, 14.1) |
| NH | — | 8.21(d, 7.4) | — | — |
| Thr | | | | |
| α | 51.89 (d) | 4.91(br d, 10.5) | 54.38 | 4.99(br d, 1.2) |
| β | 69.93 (d) | 5.10(m) | 70.37 | 5.43(m) |
| γ | 15.91 (q) | 1.17(d, 6.3) | 17.32 | 1.27(d, 6.3) |
| NH | — | 7.91(d, 8.2) | — | — |
| NMeGln | | | | |
| α | 54.94 (d) | 5.10(m) | 57.01 | 5.11(m) |
| β | 23.60 (t) | 1.99(m), 1.89(m) | 25.10 | 2.16(m) |
| γ | 31.67 (t) | 1.8–2.2 | 32.61 | 1.9–2.3 |
| NMe | 30.43 (q) | 3.02(s) | 31.63 | 3.15(s) |
| Val | | | | |
| α | 55.24 (d) | 4.38(t, 7.8) | 57.62 | 4.48(d, 8.1) |
| β | 30.00 (d) | 1.94(m) | 31.94 | 2.05(m) |
| γ | 19.24 (q) | 0.85(d, 6.8) | 19.50 | 0.96(d, 6.2) |
| δ | 17.90 (q) | 0.82(d, 6.6) | 18.85 | 0.94(d, 5.5) |
| NH | — | 7.67(d, 7.5) | — | — |
| Pro-II | | | | |
| α | 59.89$^c$ (d) | 4.20(br d, 7.2) | 62.53 | 4.39(m) |
| β | 29.70$^b$ (t) | 2.00(m), 1.92(m) | 31.17 | 2.18(m) |
| γ | 24.23 (t) | 2.00(m), 1.92(m) | 25.75 | 2.25(m), 1.99(m) |
| δ | 46.86 (t) | 3.88(m), 3.52(m) | 48.87 | 4.05(m), 3.68(m) |

TABLE 1-continued

$^{13}$C and $^1$H NMR Data for Polydiscamide A

| | DMSO-d$_6$/TFA | | CD$_3$OD | |
|---|---|---|---|---|
| | $^{13}$C | $^1$H | $^{13}$C | $^1$H |
| Asn | | | | |
| α | 48.26 (d) | 4.55(m) | not observed | 4.64(m) |
| β | 35.12 (t) | 2.46(br d, 16.1) 2.83(dd, 7.6, 16.1) | 36.22 | 2.55(br d, 15.2) 2.98(br d, 17.5) |
| NH | — | 17.28(d, 7.6) | — | — |

[a]Chemical Shift δ (multiplicity, coupling constant in Hz)
[b]may interchange
[c]may interchange Carbonyl signals: (in DMSO-d$_6$/TFA) δ 173.58, 171.86, 171.48, 171.15, 171.05, 170.80, 170.75, 170.55, 170.40 (2C), 170.32, 170.24, 169.74, 169.48, 168.85; (in CD$_3$OD) δ 177.34, 174.0 (3C), 173.75 (2C), 173.23, 173.14, 173.02, 172.90, 172.71, 172.65, 172.25, 171.46, 171.30.

EXAMPLE 4 - ANTIBACTERIAL ACTIVITY

1. Protocols

Preparation of inocula, Unless otherwise noted, all media were autoclaved at 121 C. for 15 minutes.

*Bacillus subtilis*: Standard spore stocks (ATCC strain 6633) were purchased from Difco (#0453-36-0).

2. Antibacterial Assay (MIC Method)

Two-fold dilutions of polydiscamide A were prepared in 50 μL volumes of a suitable solvent using 96-well microtiter plates. In a separate 96-well plate, 35 μL volumes of Mueller-Hinton broth were placed in each well. The compound (5 μL) was then transferred to the broth. An inoculum of *B. subtilis* in the appropriate medium was added to give a cell density of 1000 cells/mL and a total volume of 50 μL. Plates were incubated at 37 C. overnight. The MIC is the lowest concentration of the drug which completely inhibited growth.

The MIC for polydiscamide A against B. subtilis was found to be 3.1 μ/ml, a level comparable with standard antibiotics. Polydiscamide A, or a composition derived from it, may be of use as an antibiotic substance.

EXAMPLE 5 - ANTITUMOR ACTIVITY

Polydiscamide A was tested for toxicity against P388 murine leukemia cells and A549 human lung carcinoma cells.

A. Maintenance of Cell Line

P388 murine leukemia cells obtained from Dr. J. Mayo, National Cancer Institute, Bethesda, Md., and A549 cells were obtained from the American Type Culture Collection, Rockville, Md. The P388 cells were maintained in Roswell Park Memorial Institute medium 1640 (RPMI-1640) supplemented with 10% horse serum and cultured in plastic tissue culture flasks and kept in an incubator at 37 C in humidified air containing 5% CO$_2$. The A549 cells were similarly maintained in RPMI-1640 but supplemented with 10% fetal bovine serum. Antibiotic-free stock cultures of P388 and A549 cells were subcultured to 10$^5$ cells/ml by dilutions in fresh growth medium at 2 to 5 day intervals.

B. Procedure

To assess the antiproliferative effects of agents against P388 cells, 200 μl cultures (96-well tissue culture plates, Nunc, Denmark) were established at 1×10$^5$ cells/ml in drug-free medium or medium containing the crude extract at a final dilution of 1:500 or intermediate and pure compounds at 10.0, 1.0, 0.10, and 0.010 μg/ml. The solvent used for all dilutions was methanol, which was removed from all plates under vacuum. After 48 hour exposures, P388 cells were enumerated using 3-[4,5-dimethylthiazol-2-yl]-2,5-diphenyltetrazolium bromide (MTT) as described below.

To assess the antiproliferative effects of polydiscamide A or its analogs against the A549 cells, cells were established as monolayer cultures in wells of microtiter plates at a final concentration of 1.5×10$^5$ cells/ml of medium 24 hours prior to exposure to the compounds. A volume of 100 μl of medium was removed from each culture well and replaced with a volume of 100 μl of drug-free medium or medium containing the crude extract at a final dilution of 1:500 or intermediate and pure compounds at 10.0, 1.0, 0.10, and 0.010 μg/ml. Plates were incubated at 37 C for 72 hours and the cells enumerated with MTT as described below.

To quantitate the effects of polydiscamide A or its analogs on cell proliferation, 75 μl warm growth medium containing 5 mg/ml MTT was added to each well. Cultures were returned to the incubator and left undisturbed for 90 minutes. To spectrophotometrically quantitate formation of reduced formazan, plates were centrifuged (900 g, 5 minutes), culture fluids were removed by aspiration, and 200 μl of acidified isopropanol (2 ml concentrated HCl/L isopropanol) added per well. The absorbance of the resulting solutions was measured at 570 nm with a plate reader (MR700 Microplate Reader, Dynatech Laboratories, Chantilly, Va.). The absorbance of test wells was divided by the absorbance of drug free wells, and the concentration of the compound that resulted in 50% of the absorbance of untreated cultures (IC$_{50}$) was determined by linear regression of logit-transformed data. A linear relationship between P388 and A549 cell number and formazan production was found over the range of cell densities observed in this study.

C. Results

Polydiscamide A was found to have strong inhibitory properties against mouse leukemia cells and to have an IC$_{50}$ of 0.96 μg/ml. The compound was also found to have an IC$_{50}$ of 0.66 μg/ml against cultured human lung carcinoma cells (A549). The compound polydiscamide A, or a composition derived from it, may be used for inhibiting tumors in humans or in animals.

EXAMPLE 6 - ANALOGS AND VARIANTS OF THE COMPOUND

Modifications of the novel compound, polydiscamide A, can readily be made by those skilled in the art.

As used in this application, the terms "analogs," "variants" and "derivatives" refer to compounds which are substantially the same as another compound but which may have been modified by, for example, adding additional amino acids or side groups. The terms "analogs," "variants" and "derivatives" as used in this application also may refer to compounds which are substantially the same as another compound but which have atomic or molecular substitutions at certain locations in the compound.

As described, a preferred embodiment of the compound is polydiscamide A, which comprises the structure shown in FIG. 1, wherein R=Na and $R_1=R_2=R_3=$H. However, analogs or derivatives of this preferred embodiment can be readily prepared using commonly known, standard reactions. These standard reactions include, but are not limited to, methylation, acetylation, and acidffication reactions: The derivatives and analogs specifically exemplified herein can be prepared as follows:

1. Acidification. The polydiscamide A compound can be subjected to an acidification reaction to yield the structure shown in FIG. 1 wherein R=$R_1=R_2=R_3=$H. Specifically, polydiscamide A in solution undergoes acidification in the presence of HCl using standard procedures, followed by standard extraction with butanol.

2. Methylation. Polydiscamide A can be methylated using standard methylation procedures. For example, an etherial solution of excess diazomethane reacted with a solution of polydiscamide A in methanol yields the structure shown in FIG. 1, wherein $R_1=R_2=R_3=$H, and R=$CH_3$.

3. Acetylation. Acetyl (Ac) groups can be added to the $R_1$, $R_2$, and $R_3$ groups of polydiscamide A using a standard acetylation reaction. For example, acetylation of polydiscamide A can be carried out with excess acetic anhydride and pyridine (1:2), which will yield the structure shown in FIG. 1, wherein R=H and $R_1=R_2=R_3=$ Ac. This structure can be further methylareal by standard methylation procedures, as described above, and will yield the structure shown in FIG. 1, wherein R=$CH_3$ and $R_1=R_2=R_3=$Ac.

The subject invention embraces the specific structures shown for the compound and other compositions which are specifically exemplified. The subject invention further embraces analogs, variants, and derivatives of the structure, as well as analogs and variants of the derivatives. These analogs, variants, and derivatives are embraced within the subject invention so long as the analog, variant, or derivative retains substantially the same relevant biological activity as the originally exemplified compound. For example, it is well within the skill of a person trained in this art to make atomic or molecular substitutions. To the extent that these substitutions do not substantially alter the relevant biological or chemical activity, then the resulting compounds fall within the scope of the subject invention. The term "relevant biological or chemical activity" refers to the activity of interest for a particular application of a compound. For example, several uses of polydiscamide A are discussed herein. These uses include inhibition of bacterial and cellular growth. When polydiscamide A is being used in these ways, then "analogs" would refer to compounds where polydiscamide A has been modified (by a molecular substitution, for example) without substantially altering the compound's ability to inhibit bacterial or cellular growth. Molecular substitutions are only one example of the type of modifications which are within the scope of the subject matter of this invention.

EXAMPLE 7 - FORMULATION AND ADMINISTRATION

The compounds of the invention are useful for various non-therapeutic and therapeutic purposes. It is apparent from the testing that the compounds of the invention are effective for inhibiting bacterial growth and for controlling tumor growth. Also, because of the antibacterial properties of the compounds, they are useful to swab laboratory benches and equipment in a microbiology laboratory to eliminate the presence of bacteria, or they can be used as ultraviolet screeners in the plastics industry since they effectively absorb UV rays. As disclosed herein, they are also useful prophylactically and therapeutically for treating bacterial infections in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A process for treating a human or animal hosting cancer cells, said process comprising administering to said human or animal a cancer cell inhibiting amount of a compound having the structure shown in FIG. 1, wherein R is Na, H, or $CH_3$; and $R_1$, $R_2$, and $R_3$ are H or Ac.

2. The process, according to claim 1 wherein R is Na.

3. The process, according to claim 1 wherein R is H.

4. The process, according to claim 1 wherein R is $CH_3$.

5. The process, according to claim 1, wherein R is Na and $R_1$, $R_2$, and $R_3$ are H.

* * * * *

UNITED STATES PATENT AND TRADEMARK OFFICE
CERTIFICATE OF CORRECTION

PATENT NO. : 5,516,755
DATED : May 14, 1996
INVENTOR(S) : Nanda K. Gulavita, Sarath P. Gunasekera, Shirley A. Pomponi, Ross E. Longley, Peter J. McCarthy It is certified that error appears in the above-indentified patent and that said Letters Patent is hereby corrected as shown below:

Column 3: Line 36: "potydiscus" should read --polydiscus--.
Column 4: Line 38: "Compund" should read --Compound--.
Column 7: Table 1, Last line : "17.28(d, 7.6)" should read --7.28 (d, 7.6)--;
   Line 43: "3.1 µ/ml," should read --3.1 µg/ml,--.
Column 9: Line 14: "acidffication" should read --acidification--;
   Line 33: "methylareal" should read --methylated--.

Signed and Sealed this

Seventeenth Day of September, 1996

Attest:

BRUCE LEHMAN

*Attesting Officer*   Commissioner of Patents and Trademarks